United States Patent [19]

Sakai et al.

[11] Patent Number: 4,765,340

[45] Date of Patent: Aug. 23, 1988

[54] APNEA DETECTOR

[75] Inventors: Takao Sakai, Habikino; Kenji Hamaguri, Osaka, both of Japan

[73] Assignee: Minolta Camera Kabushiki Kaisha, Osaka, Japan

[21] Appl. No.: 847,313

[22] Filed: Apr. 2, 1986

[30] Foreign Application Priority Data

Apr. 2, 1985 [JP] Japan .................................. 60-69690

[51] Int. Cl.$^4$ ................................................ A61B 5/00
[52] U.S. Cl. ..................... 128/633; 128/716; 356/41
[58] Field of Search ............... 128/633, 634, 664, 665, 128/666, 716, 719; 340/573, 575; 356/41

[56] References Cited

U.S. PATENT DOCUMENTS

| | | | |
|---|---|---|---|
| 3,734,091 | 5/1973 | Taplin | 128/633 X |
| 4,146,885 | 3/1979 | Lawson, Jr. | 340/573 |
| 4,245,651 | 1/1981 | Frost | 128/721 |
| 4,305,400 | 12/1981 | Logan | 128/670 |
| 4,350,166 | 9/1982 | Mobarry | 128/664 |
| 4,403,215 | 9/1983 | Hofmann et al. | 340/573 |
| 4,450,843 | 5/1984 | Barney et al. | 128/690 |
| 4,523,279 | 6/1985 | Sperinde et al. | 356/41 X |

FOREIGN PATENT DOCUMENTS 3134124  3/1983  Fed. Rep. of Germany ...... 128/633

OTHER PUBLICATIONS

Yelderman et al., "Real Time Oximetry", *Computing in Anesthesis and Intensive Care,* Martinus Nyhoff, Pub. 1983.

Krauss et al., "Noninvasive Estimation . . . Infants", The J. Pediatrics, vol. 93, No. 2, pp. 275–278, 1978.

*Primary Examiner*—Lee S. Cohen
*Attorney, Agent, or Firm*—Price, Gess & Ubell

[57] ABSTRACT

A medical apparatus for detecting apnea, in particular, in infants and children. The apparatus measures oxygen saturation in the blood and relates the measurement to a normal condition. The relationship is employed to indicate apnea.

8 Claims, 16 Drawing Sheets

4,765,340

APNEA DETECTOR

BACKGROUND OF THE INVENTION

1. Field of the Invention

The present invention relates to medical apparatus for detecting apnea, in particular, in infants or children.

2. Description of the Prior Art

There have been, in the past, apnea detectors for detecting various respiratory impedances in children known in U.S. Pat. Nos. 4,403,215 and 4,305,400, and apnea detectors for detecting cessation of body movements during respiration known in U.S. Pat. Nos. 4,146,885 and 4,245,651. There apparatus have, however, problems with reliability, because they cannot detect such apnea where only respiration exists but no gas exchange takes place.

SUMMARY OF THE INVENTION

An object of the present invention is to provide an apnea detector which is capable of solving such a problem and detecting apnea promptly with high reliability.

In order to achieve said object, an apnea detector according to the present invention is characterized in comprising means for measuring oxygen saturation in the blood, means for memorizing the oxygen saturation characteristic of a normal condition, means for detecting excessive reduction of oxygen saturation to produce a detecting signal when the measured oxygen saturation is reduced under a predetermined amount from the memorized oxygen saturation and means for detecting apnea in accordance with said detecting signal. As the apparatus according to the present invention detects excessive reduction of oxygen saturation in the blood as apnea by said composition, when such excessive reduction is more than the predetermined amount compared with the oxygen saturation in a normal condition, it can detect apnea in a case when only respiration takes place and no gas exchange is realized, thus providing a higher reliability and quicker response as the measurement of oxygen saturation can be made in a short time.

BRIEF DESCRIPTION OF THE DRAWINGS

These and other objects and features of the present invention will become apparent from the following description taken on conjunction with preferred embodiments thereof with reference to the accompanying drawings, throughout which like parts are designated by like reference numerals, and in which.

DETAILED DESCRIPTION OF THE PREFERRED EMBODIMENTS

Figure 1:
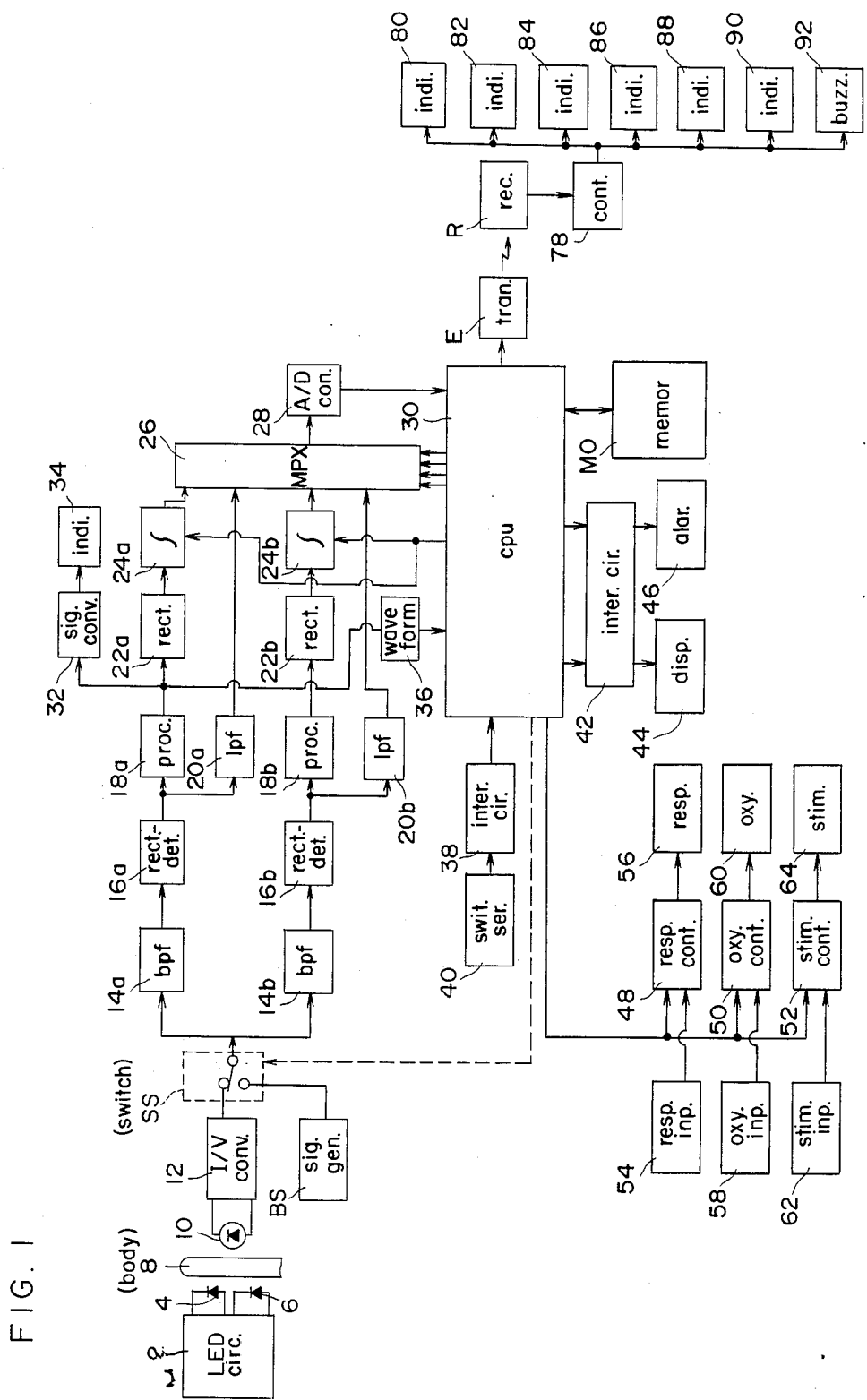
FIG. 1 is a block diagram illustrating the first example of embodiment of the present invention.

Before descriptions proceed to the preferred embodiments of the present invention, the theory of measuring oxygen saturation for detecting apnea is given hereunder.

Light incident on a human body is absorbed and scattered by the blood and muscles, thus the intensity of the incident light is decreased. Since arterial blood is pulsating and its volume changes cyclically, the quantity of light transmitted through the body also changes cyclically. If $I\lambda$ is the intensity of light transmitted through the body with respect to wavelength $\lambda$, $$I\lambda = Io\lambda \cdot Ft\lambda \cdot Fv\lambda \cdot f(\mu\lambda) e^{-g(\mu\lambda)(d+\Delta)} \qquad (1)$$

wherein, $Io\lambda$ is the intensity of incident light with wavelength $\lambda$, $Ft\lambda$ is the transmittance at bloodless regions of the body, $Fv\lambda$ is the transmittance of venous blood, $\mu\lambda$ is an absorption coefficient of the arterial blood with the light of wavelength of $\lambda$, $f(\mu\lambda)$ and $g(\mu\lambda)$ are functions of wavelengths $\mu$ and $\lambda$ respectively, d is the averaged thickness of arterial blood, and $\Delta d$ is the change in thickness which varies periodically according to beat of the heart.

A DC component $Y\lambda$ in the logarithmically compressed value of $I\lambda$ can be given as follows:

$$Y\lambda = -g(\mu\lambda)d \qquad (2)$$

As $g(\mu\lambda)$ is approximately proportional to the square root of $(\mu\lambda)$, $$Y\lambda^2 = k\lambda\mu\lambda(\Delta d)^2 \qquad (3)$$

where $k\lambda$ is a constant to be determined dependent on the wavelength $\lambda$. The absorption coefficient $\mu\lambda$ can be given by the following formula:

$$\mu\lambda = CHbo_2 \cdot E\lambda Hbo_2 + CHb \cdot E\lambda Hb \qquad (4)$$
$$= Ct\{S(E\lambda Hbo_2 - E\lambda Hb) + E\lambda Hb\}$$

Where $CHbo_2$ and $CHb$ are concentrations of oxyhemoglobin and deoxyhemoglobin, respectively, $Ct = CHbo_2 + CHb$, $S = CHbo_2/Ct$, $E\lambda Hbo_2$ and $E\lambda Hb$ are absorption coefficients of oxyhemoglobin and deoxyhemoglobin against the light of wavelength $\lambda$, respectively. Accordingly, $Y\lambda^2$ can be given as follows:

$$Y\lambda^2 = k\lambda Ct\{S(E\lambda Hbo_2 - E\lambda Hb) + E\lambda Hb\}(\Delta d)^2 \qquad (5)$$

By obtaining $Y\lambda$ at 2 different wavelengths $\lambda_1$ and $\lambda_2$, S can be attained as follows:

Since $$(Y\lambda_1)^2 = k\lambda_1 Ct\{S(E\lambda_1 Hbo_2 - E\lambda_1 Hb) + E\lambda_1 Hb\}(\Delta d)^2$$

$$(Y\lambda_2)^2 = k\lambda_2 Ct\{S(E\lambda_2 Hbo_2 - E\lambda_2 Hb) + E\lambda_2 Hb\}(\Delta d)^2,$$

and $$S = - \qquad (6)$$

-continued
$$\frac{E\lambda_2 Hb \cdot \frac{Y\lambda_1^2}{k\lambda_1} - E\lambda_1 Hb \cdot \frac{Y\lambda_2^2}{k\lambda_2}}{(E\lambda_2 Hbo_2 - E\lambda_2 Hb) \cdot \frac{Y\lambda_2}{k\lambda_1} - (E\lambda_1 Hbo_2 - E\lambda_1 Hb) \cdot \frac{Y\lambda_2^2}{k\lambda_2}}$$

By applying the light with wavelength of $\lambda_1$ which satisfies an equation of $E\lambda_1 Hbo_2 = E\lambda_1 Hb$, the above equation (6) can be expressed as follows:

$$S = \frac{k\lambda_1}{k\lambda_2} \cdot \tag{7}$$

$$\frac{E\lambda_1 Hb}{E\lambda_2 Hbo_2 - E\lambda_2 Hb} \cdot \left(\frac{Y\lambda_2}{Y\lambda_1}\right)^2 - \frac{E\lambda_2 Hb}{E\lambda_2 Hbo_2 - E\lambda_2 Hb}$$

Since the oxygen saturation (hereinafter simply abbreviated as SaO2) can be defined as $SaO_2 = S \times 100$ (%), the equation (7) can be as follows:

$$SaO_2 = A \times (Y\lambda_2/Y\lambda_1)^2 + B \tag{8}$$

wherein A and B are constants determined by optical properties of the blood.

FIG. 1 illustrates a block diagram showing composition of a first embodiment according to the present invention. In this figure, LED lighting circuit (2) is to light LEDs (4) and (6), each having a different illuminating wavelength $\lambda_1$ and $\lambda_2$ respectively, continuously with alternating current with different frequencies $f_1$ and $f_2$ respectively. The light illuminated from LEDs (4) and (6) and transmitted through a body (8) is converted to electrical signals by a light receiving element (10). A photoelectric current-voltage converter (12) converts the current output from said light receiving element (10) to the corresponding voltage. (14a) and (14b) are band pass filters, of which central frequencies are $f_1$ and $f_2$, for picking up signals equivalent to the intensity of light transmitted through the body (8) out of said current-voltage converter (12). Input to band pass filters (14a) and (14b) can be shifted to the standard signal generating section (BS) by a selector switch.

Rectifying-detecting sections (16a) and (16b) detect and modulate outputs from the band pass filters (14a) and (14b), and then output signals corresponding to the optical properties of the body (8) at wavelength zones $\lambda_1$ and $\lambda_2$. Processing sections (18a) and (18b) calculate the ratio of AC component against DC component of outputs from rectifying-detecting sections (16a) and (16b), respectively. The outputs from rectifying-detecting sections (18a) and (18b) are also input into low pass filters (20a) and (20b) respectively. Full-wave rectifiers (22a) and (22b) rectify outputs from the processing sections (18a) and (18b). Sphygmic wave integrating sections (24a) and (24b) integrate ouputs from the full-wave rectifying sections (22a) and (22b) according to controls by central processing unit (CPU) (30). An analog multiplexer (26) selects either one of outputs from sphygmic wave integrating sections (24a) and (24b) and low pass filters (20a) and (20b) and inputs it into A/D converting section (28). A/D converting section (28) converts the selected signal into a digital signal, which is in turn input to CPU (30). Sphygmic signal converting section (32) converts an output from processing section (18a) to a signal suitable for inputting to sphygmic indicator (34). Output from processing section (18a) are converted to the form of a pulsating wave at pulsating wave forming section (36) and then input to CPU (30).

CPU (30) calculates SaO2 from outputs of A/D converting section (28) and makes a calculation of pulse rate from the output of sphygmic wave forming section (36) as well as detection of apnea and judgement of recovery from apnea. CPU (30) also controls sphygmeric wave integrating sections (24a) and (24b), analog multiplexer (26) and input selector switch (SS). In addition, data set at switch setting section (40) are input into CPU (30) through interface circuit (38). CPU (30) further controls and drives displaying section (44) and alarm section (46) through interface circuit (42), and transmits evaluated results of apnea to artificial respiration control section (48), oxygenator control section (50) and patient stimulator control section (52). The apparatus of the first embodiment according to the present invention employs a microcomputer at CPU (30). Said components from (2) to (30) except the body (8) are to calculate the amount of SaO2 or its equivalent but they can be replaced with any one of other types of oximeter. It may be a Wood type or a multi-wavelength ear type oximeter which measures the arterial blood, but an apparatus which measures venous blood may be used.

Displaying section (44) displays, as explained later, the amount of SaO2 and that of pulse rate in normal conditions, required detecting condition for diagnosing as apnea, required detecting condition for diagnosing as recovery from apnea, the total numbers of apnea states and the accumulated time of apnea as well as the measured amount of SaO2 and measured pulse rate. Alarm section (46) indicates an alarm in cases where apnea has been detected, determination of apnea becomes faulty or incapable, AC power source (76) has been replaced with a built-in battery (68) due to power interruption of AC power source (76), or voltage output of the built-in battery (68) has been lowered. Interface circuit (42) controls and drives display section (44) and alarm section (46) according to the commands of CPU (30). Switch setting section (40) sets constants to be used at CPU (30) for detecting apnea and recovery from apnea. The set constants are input into CPU (30) through the interface circuit (38), displayed at displaying section (44) and memorized by memory section (MO).

Respirator control section (48) provides control of respirator (56) in accordance with a decision on apnea made at CPU (30), in a condition in which a mode setting switch provided at respirator input section (54) has been turned on, as stated later.

Oxygenator control section (50) controls oxygenator (60) in accordance with a decision on SaO2 amount and apnea made at CPU (30), in a condition in which a mode setting switch provided at oxygenator input section (58) has been turned on, as described later. Patient stimulator control section (52) controls a patient stimulator (64) according to decision of apnea made at CPU (30), in a condition in which a mode setting switch provided at patient simulator input section (62) has been turned on, as explained later.

Figure 2:
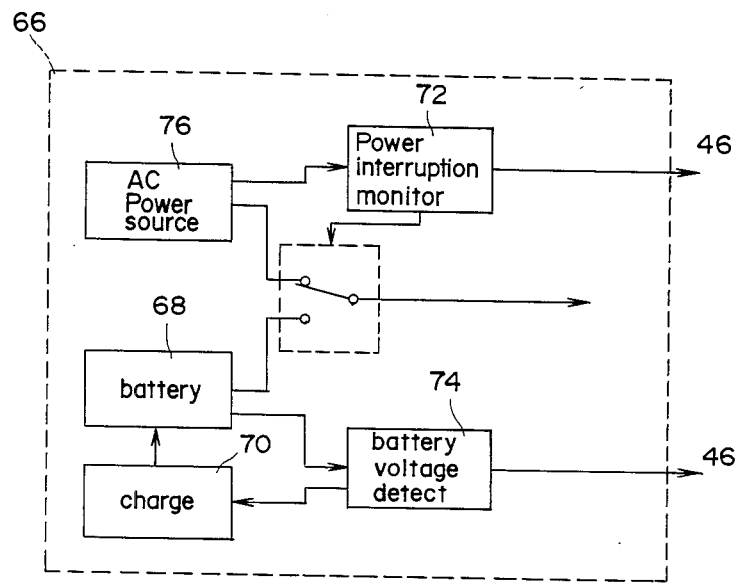
FIG. 2 is a block diagram illustrating composition of power source.

FIG. 2 is a block diagram illustrating composition of the power supply section (66) provided for supplying electric power to each of the circuits. Power supply section (66) consists of a built-in battery (68), battery charging section (70), interruption monitoring section (72), and battery voltage detecting section (74). (76) shows an AC power source. Interruption monitoring section (72) monitors voltage outputs of the AC power source (76) and shifts the power supply from the AC power source (76) to the built-in battery (68) in case of power interruption. Battery charging section (70) charges the built-in battery (68) while AC power is supplied to each circuits from the AC power source (76). Battery voltage detecting section (74) monitors voltage output from built-in battery (68), and gives an alarm from alarm section (46), when the monitored voltage level has dropped.

Referring back to FIG. 1, transmitter (E) transmits signals corresponding to the amount of $SaO_2$ and pulse rate calculated by the CPU (30) and to other alarm information, through wire or wireless means. Receiver (R) receives signals transmitted from transmitter (E). Display and alarm controller (78) controls and drives $SaO_2$ indicator (80), pulse rate indicator (82), apnea alarm indicator (84), inoperation alarm indicator (86) power interruption alarm indicator (88), battery voltage drop alarm indicator (90) and alarm buzzer (92).

Figure 3:
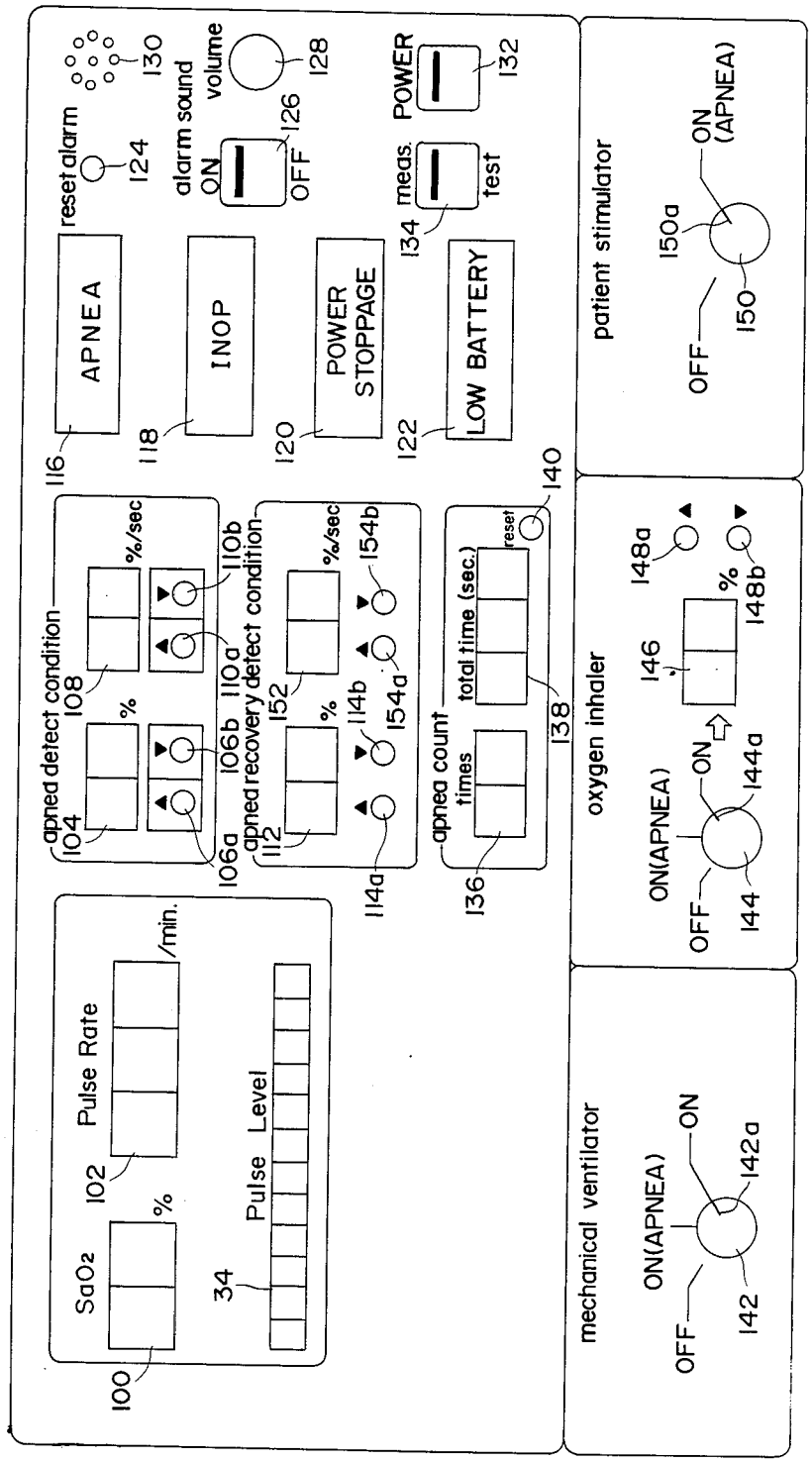
FIG. 3 is a schematic view illustrating composition of display section, alarm section, and switch input section.

FIG. 3 shows the composition of display section (44), alarm section (46) and switch setting section (40) of the first embodiment of the present invention. In FIG. 3, (100) is a $SaO_2$ indicating element which indicates the latest measured oxygen saturation in a digital value, (102) is pulse rate indicating element which indicates the measured pulse rate in a digital value, and (34) is the sphygmic indicator. (104) is an element for indicating the lower limit of $SaO_2$ in a digital value to detect apnea, and the lower limit of $SaO_2$ can be manually set by means of operation of an increment button (106a) and a decrement button (106b). (108) is an element for indicating the maximum limit of $SaO_2$ lowering speed in a digital value to detect apnea, and the maximum limit of $SaO_2$ lowering speed can be manually set by operating an increment button (110a) and a decrement button (100b). (112) is an element for indicating the limit of $SaO_2$ in a digital value to detect recovery from apnea, and the limit of $SaO_2$ can be manually set by operating an increment button (114a) and a decrement button (114b). Furthermore, (152) is an element for indicating the limit of $SaO_2$ increasing speed in a digital value to detect recovery from apnea, and the limit of $SaO_2$ increasing speed (rate) can be set by manipulating an increment button (154a) and a decrement button (154b).

(116) is an alarm element to give an alarm when apnea has been detected. (118) is an alarm element to give an alarm by lighting an alarm lamp when it has been detected that the apparatus does not operate. (120) is an alarm element to give an alarm by lighting a lamp when power interruption of AC power source (76) has been detected, and (122) is an alarm element to give an alarm by lighting a lamp when the voltage of built-in battery (68) has dropped lower under a predetermined level. (124) is an apnea alarm reset switch, the operation of which allows a manual reset of the alarm element for apnea (116). (126) is an alarm buzzer release switch to stop the buzzer for sounding. (128) is a volume controller to adjust the sounding volume of the alarm buzzer, and (130) is a speaker for sounding the alarm.

(132) is a main switch for the power supply. (134) is a mode selecting switch for selecting one of the modes between a test mode and a measuring mode both of which will be explained later.

(136) is an element to indicate the detected number of apnea in a digital value, while (138) is an element to indicate the accumulated time of apnea in a digital value. The counting of such number and accumulated time can be reset by manipulating a reset switch (140).

(142) is a mode setting switch for respirator (56) and is included in respirator input section (54) as shown in FIG. 1. Respirator (56) does not work, when an index (142a) of the mode setting switch (142) is set on the index "OFF", even if CPU (30) detects an apnea. The respirator (56) works when apnea has been detected by CPU (30), if the index (142a) is set on the index "ON (APNEA)". If the index (142a) is set on the index "ON", respirator (56) can be operated regardless of the detection of apnea by CPU (30).

Items from (144) to (148b) are included in oxygenator input section (58) of FIG. 1, wherein (144) is a mode setting switch for oxygenator (60), (146) is an element for indicating the limit of $SaO_2$ which becomes the working level of oxygenator (60) with respect to $SaO_2$ when index (144a) of switch (144) is set on the index "ON". Here, the limit value indicated in the element (146) can be set by operating an increment button (148a) or a decrement button (148b). When index (144a) of switch (144) is matched with the index "OFF", the oxygenator (60) does not work even if apnea is detected by CPU (30). When index (144a) is matched with the index "ON(APNEA)", oxygenator (60) can be operated upon detection of apnea by CPU (30). If the index (144a) is set on the index "ON", oxygenator (60) can be operated regardless of the detection of apnea by CPU (30), when the measured $SaO_2$ becomes less than the value indicated by the element (146).

(150) is a mode setting switch for patient stimulator (64), and the switch (150) is included in patient stimulator input section (62). Patient stimulator (64) does not work, when index (150a) of the switch (150) is set on the index "OFF", even if CPU (30) detects apnea. Patient stimulator (64) works when apnea has been detected by CPU (30), if the index (150a) is set on the index "ON (APNEA)". Here, patient stimulator (64) is a device to give stimulations to the patient by tapping the sole of his foot for recovery of respiration.

Next the operation of this embodiment is explained. LED lighting circuit (2) is to energize the LEDs (4) and (6) having different luminous wavelength bands $\lambda_1$ and $\lambda_2$ respectively with different frequencies $f_1$ and $f_2$ which are sufficiently higher than the sphygmic frequency of the body (8). Light receiving element (10) converts the intensity of light, which was emitted from LEDs (4) and (6) and has passed through the body (8), into electric signals. Here, the light which has passed through the body (8) is the light emitted from LEDs (4) and (6) and amplified and modulated according to optical properties at wavelengths $\lambda_1$ and $\lambda_2$. Photoelectric current of light receiving element (10) is converted to voltage by the photoelectric current-voltage converting section (12). As central frequency of band pass filters (14a) and (14b) is $f_1$ and $f_2$ respectively, they separate signals only equivalent to the light which has been emitted from LEDs (4) and (6) and has passed through the body (8). Rectifying and detecting sections (16a) and (16b) detect outputs from band pass filters (14a) and (14b) and demodulate signals to handle the optical properties of the body (8) at wavelength bands $\lambda_1$ and $\lambda_2$. Outputs of rectifying and detecting sections (16a) and (16b) are input to processing sections (18a) and (18b) and low pass filters (20a) and (20b), and signals equivalent to the equation (2) are output from respective processing section (18a) and (18b). These signals correspond to the sphygmic signals of photoelectric volume at wavelengths $\lambda_1$ and $\lambda_2$ of the measuring part, and have been output as the result of volumetric changes in the arterial blood at the measured region by heart beats.

Full-wave rectifying sections (22a) and (22b) are composed of a half wave rectifying circuit and a differential amplifier, and rectifies outputs of processing sections (18a) and (18b). At sphygmic integrating sections (24a) and (24b), outputs of full-wave rectifying sections (22a) and (22b) are integrated for a predetermined period under the control of control processing section (30), and results thereof are stored for a certain period. These stored outputs of sphygmic integrating sections (24a) and (24b) and outputs of low pass filters (20a) and (20b) are selected by analog multiplexer (26) in turn and are input into A/D converter (28). It is controlled by control processing section (30) which input analog multiplexer (26) will select. A/D converter (28) converts the selected input into digital value under the control of by control processing section (30).

Outputs from low pass filters (20a) and (20b) are converted from analog to digital values in the A/D converter (28) through analog multiplexer (26), and are used for checking whether the luminous intensity have been emitted from LEDs (4) and (6) and transmitted through the body (8) in a proper manner or not. This is because the accuracy of sphygmic processing may be deteriorated by saturation of the light receiving element (10) or the photoelectric current-voltage converting section (12), when the received light intensity of light receiving element (10) is very large. Contrary, in the case when the received light intensity of light receiving element (10) is very small, properties of light receiving element (10) or photoelectric current-voltage converting section (12) would be deteriorated, and then accurate sphygmic processing becomes impossible. Therefore, control processing section (30) monitors if the luminous intensity is proper or not by A/D converting outputs from low pass filters (20a) and (20b).

In addition, control processing section (30) monitors the ratio of outputs of low pass filter (20a) against outputs of low pass filter (20b). This is because the output ratio of low pass filter (20a) against low pass filter (20b) changes in accordance with the change of $SaO_2$. Then, the monitored output ratio of low pass filter (20a) against low pass filter (20b) is compared with a normal ratio stored in the memory section (MO), in the CPU (30). The CPU (30) operates the alarm section (46) when the difference between the monitored ratio and the normal ratio is over a predetermined amount. Accordingly, the output ratio of low pass filter (20a) and (20b) can detect apnea, in case apnea cannot be detected from $SaO_2$ amount from the sphygmic waves for some reason, thus giving a high reliability to the apparatus under the present invention.

Sphygmic integrating sections (24a) and (24b) repeat the integration, storing and discharge at a fixed cycle and outputs of these sections are converted from analog signals to digital signals in turn together with outputs of low pass filters (20a) and (20b). Oxygen saturation ($SaO_2$) can be calculated at control processing section (30) by the prescribed processing from amplified sphygmic values obtained from said A/D conversion of outputs from sphygmic integrating sections (24a) and (24b). Sphygmic signal converting section (32) converts the output of processing section (18a) to a form suitable for inputting to sphygmic indicator (34). Sphygmic indicator (34) is provided to confirm whether sphygmic signals are normally obtained or not. Pulse wave forming section (36) converts an output of processing section (18a) to pulse signals in 2 digits with a fixed limit, which are in turn input to control processing section (30). Control processing section (30) detects positive edges and negative edges of these input pulse waves, and calculates pulse rate per minute from reciprocal numbers of frequencies obtained. Calculation of pulse rate is repeated at a fixed interval like the calculation of $SaO_2$.

When $SaO_2$ has dropped lower than a predetermined lower limit, the patient is considered to be in the state of apnea and is in need of a certain treatment. In this embodiment, certain values preset by switch setting section (40) are employed as the maximum limit of $SaO_2$ lowering speed and the lower limit of $SaO_2$, in order to detect apnea. Control processing section (30) makes a decision of apnea, when $SaO_2$ being measured repeatedly at a certain frequency has dropped faster than the maximum limit preset on the indicating element (108), or when the measured $SaO_2$ has dropped lower than the limit preset on the indicating element (104). When apnea has been detected, apnea alarm element (116) shown in FIG. 3 is energized and an alarm is sounded through speaker (130). The alarm sound can be cut off by the operation of the alarm sound switch (126).

The patient is considered to have been relieved from apnea and to have begun to respire again, when his $SaO_2$ has returned to the normal value or his $SaO_2$ increasing speed is faster than the predetermined limit. In this embodiment, the value preset by switch setting section (40) and indicated on indicating element (112) is employed as $SaO_2$ value showing the recovery from apnea, and the value preset by switch setting section (46) and indicated on indicating element (152) is employed as the $SaO_2$ increasing speed showing it. In case the measured $SaO_2$ has returned to the value preset on indicating element (112) or higher, or the measured $SaO_2$ increasing speed has returned to the speed preset on indicating element (152) or higher, control processing section (30) makes a decision of recovery from apnea, while alarm section (48) turns off apnea alarm element (116) and an alarm sound from speaker (130) also ceases. Apnea alarm sound also be manually stopped by switch (126).

Figure 4:
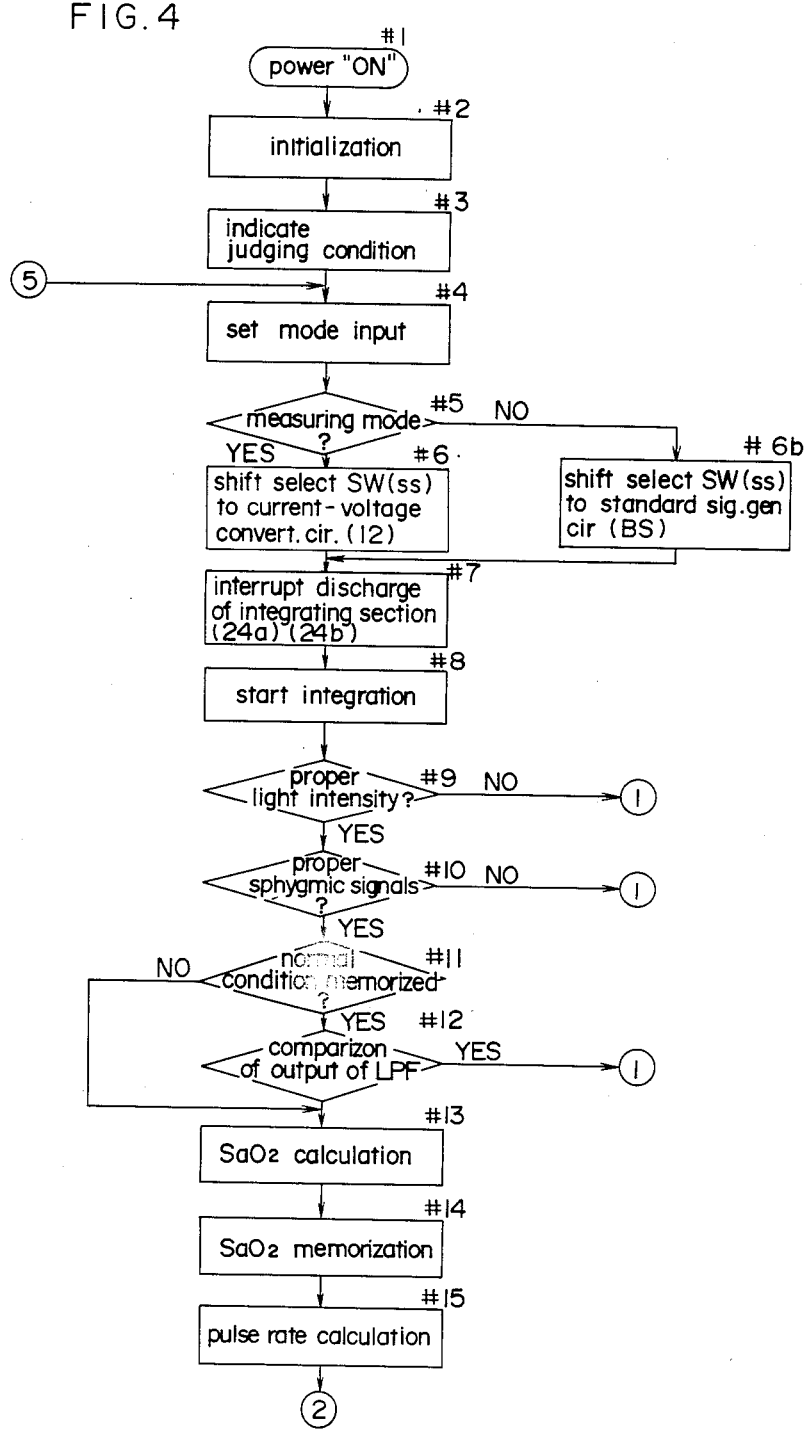
FIGS. 4–14 are flow charts showing their respective movements.

Next, operation of control processing section (30) in this embodiment is explained in detail with presentation of flow charts FIGS. 4–14. In FIG. 4, when power switch (132) is turned on at #1, the system is initialized at (#2), the value predetermined by manual operation is set as a necessary requirement for detection of apnea, and the value for recovery from apnea is at #3. These values are memorized in memory section (MO). In this embodiment, manually set values are employed as the lower limit of $SaO_2$ and the maximum limit of the $SaO_2$ lowering speed for detecting apnea, and the lower limit of $SaO_2$ and the minimum limit of $SaO_2$ increasing speed for detecting recovery from apnea, and they are indicated on the indicating elements (104), (108), (112) and (152) of display section (44), respectively. These preset values can be changed by operating buttons (106a), (106b), (110a), (110b), (114a), (114b), (154a) and (154b). For instance, if setting button (106a) is kept pressed, the lower limit of $SaO_2$ for detecting apnea which is stored in memory section (MO) is increased for each predetermined time intervals, and the indication by indicating element (104) varies. However, if setting button (106b) is kept pressed, the lower limit of $SaO_2$ decreases, and the indication by indicating element (104) varies. Operation of other buttons (110a), (110b), (114a), (114b), (154a) and (154b) can be made in similar ways.

At #4, the setting mode of mode selecting switch (134) is input to the CPU (30), and the setting mode is discriminated at #5. When the setting mode of the mode selecting switch (134) is the measured mode (meas), #5 is branched to #6a, while if the mode is set to the test mode (test) side, it is branched to #6b. Operation in the measuring mode is explained hereunder. In the measuring mode (meas), selector switch (SS) for selecting the input to the band pass filters (14a) and (14b) is shifted to the side which directs selection of outputs from photoelectric current-voltage converting section (12) at #6a. Then, control processing section (30) stops discharges of sphygmic wave integrating sections (24a) and (24b) at #7, and starts integration of both full-wave rectifying sections (22a) and (22b) at #8. Control processing section (30) completes integration of sphygmic wave integrating section (24a) and (24b) in the prescribed time and stores respective output. In the next place, control processing section (30) controls analog multiplexer (26) and converts outputs from sphygmic wave integrating sections (24a) and (24b) and outputs from low pass filters (20a) and (20b) to digital signals at A/D converting section (28). These converted digital signals are input into control processing section (30) and utilized for calculation of $SaO_2$. Upon completion of A/D conversion, respective integrating capacitors of sphygmic wave integrating sections (24a) and (24b) are discharged. Start and completion of integrating said sphygmic wave, storing of outputs, A/D conversion and discharge of capacitors are repeated at fixed intervals.

Figure 6:
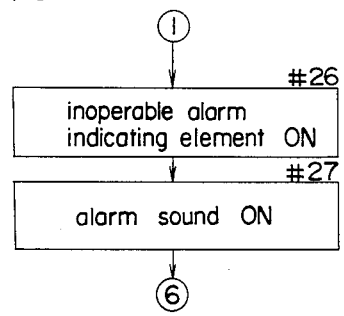

Digital signals obtained at A/D converting section (28) are utilized for $SaO_2$ calculation during integration at sphygmic wave integrating section (28) in the following cycle. Control processing section (30) makes decision on whether A/D converted values of outputs from low pass filters (20a) and (20b) are within the prescribed ranges or not, and then confirms that the luminous intensity is proper at #9. When the luminous intensity has been judged improper, the program is jumped to #28 as shown in FIG. 6, and the inoperation alarm element (118) is illuminated, while the alarm sound is generated from speaker (130) at #27. When the above values have been judged proper at #9, the program of CPU (30) proceeds to #10 and the sphygmic signals are checked whether the levels of the sphygmic signals are proper or not. If sphygmic signals have been judged improper, the program is separated to #26 of FIG. 8. When sphygmic signals are proper at #10, the program proceeds to #11 and a normal condition memorizing flag is examined for discriminating whether memorization of outputs from low pass filters (20a) and (20b) in normal condition is taking place or not. If not, they should proceed to #13. When memorization of normal condition is taking place, a comparison of the output ratios in low pass filters (20a) and (20b) between measured values and memorized values of normal condition is to be made. If changes in those ratios are more than the prescribed, the program should be separated to #28 of FIG. 6.

At #13, $SaO_2$ can be calculated from the A/D converted values of outputs from sphygmic wave integrating section (24a) and (24b) according to the prescribed formula. $SaO_2$ value obtained is memorized in the $SaO_2$ table of memory section (MO) at #14, which table stores a predetermined number of the calculated $SaO_2$ value from the latest one in sequence. A value averaging the latest predetermined number of calculated $SaO_2$ values is picked up as the present $SaO_2$ value.

Next, the pulse rate is calculated at #15. The pulse rate is calculated from the time interval of positive edges in pulse output of sphygmic wave forming section (36). The positive and negative edges of pulse output from sphygmic wave forming section (36) are checked at all times by control processing section (30) and the time of positive edges and the time of negative edges are memorized in order. The pulse rate per a minute is calculated based on the positive and negative edges of the latest predetermined number of the pulses.

Figure 5:
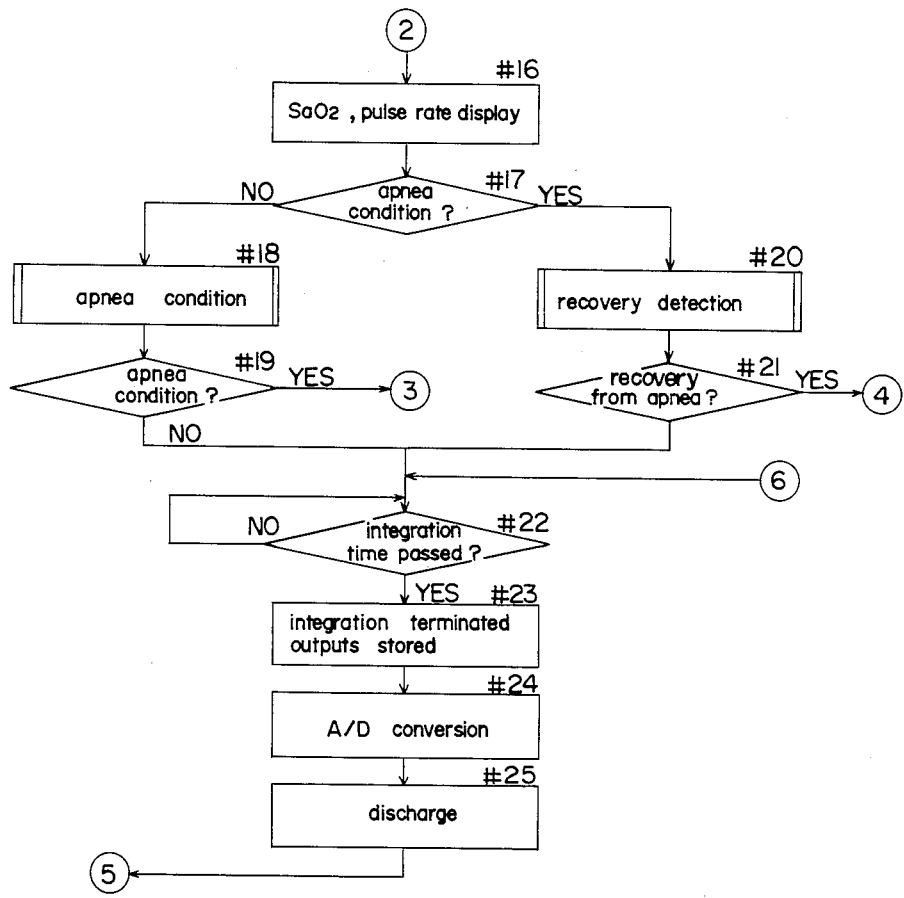

The calculated $SaO_2$ and the calculated pulse rate are displayed on $SaO_2$ indicating element (100) and on pulse rate indicating element (102) respectively at #16 of FIG. 5. Then, an apnea flag of memory section (MO) is checked at #17, and if apnea condition is not detected, the program proceeds to #18 and enters the apnea detection subroutine for detecting apnea. If an apnea exists condition is detected at #17, the program proceeds to #20 and enters the recovery detection subroutine which judges whether recovery from apnea has been made or not.

Figure 7:
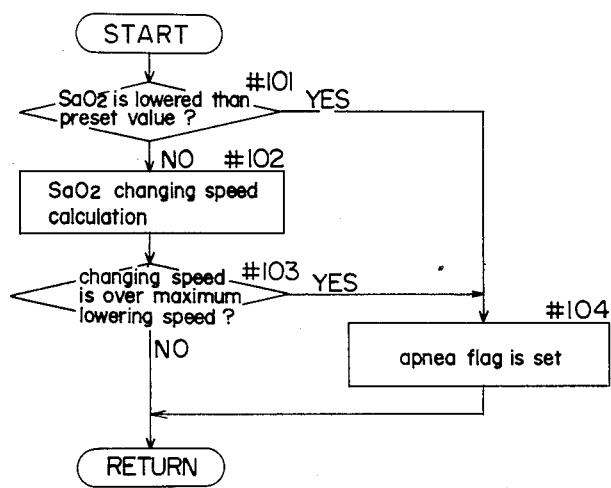

In this embodiment, detection of apnea as shown in #18 carried out on the basis of a flow chart in FIG. 7 as follows. First, the present $SaO_2$ is compared with the lower limit of $SaO_2$ for detecting apnea as shown on indicating element (104) at #101. The program is separated to #104 and an apnea flag is set, if the present $SaO_2$ is judged as less than the lower limit. The program proceeds to #102, when the present $SaO_2$ is judged at #101 as more than the lower limit. Here, the $SaO_2$ changing speed is calculated from the last $SaO_2$ memorized in the $SaO_2$ memorizing table and the $SaO_2$ which was measured by the previous prescribed cycles. At #103, a comparison of the obtained $SaO_2$ changing speed with the maximum limit of $SaO_2$ lowering speed set in indicating element (108) for detecting apnea is carried out, and the program is separated to #104 and the apnea flag is set when $SaO_2$ has dropped in speed higher than the said speed limit.

Figure 8:
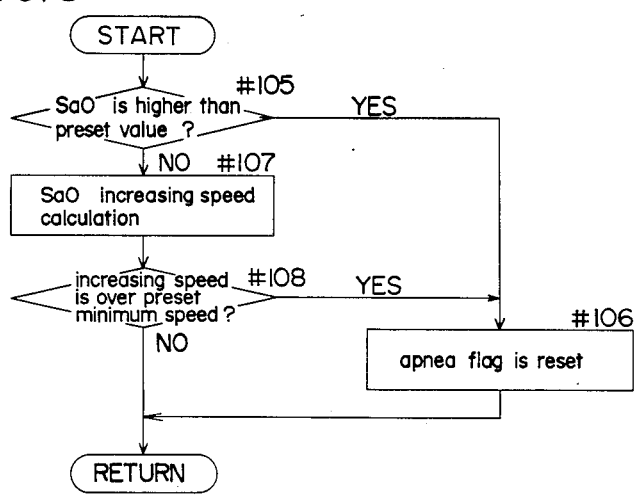
Figure 9:
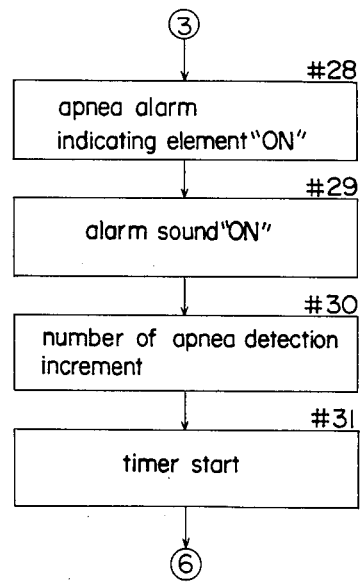

However, detection of recovery from apnea in this embodiment as shown in #20 of FIG. 5 is made on the basis of a flow chart of FIG. 8. In FIG. 8, a comparison of the present $SaO_2$ with the limit of $SaO_2$ indicated on indicating element (112) for detecting recovery from apnea is made at #105. When the present $SaO_2$ is higher than the limit, the program is separated to #108 and the apnea flag is reset. When the present $SaO_2$ is less than the limit, the program proceeds to #107. At #107, the $SaO_2$ increasing speed is calculated from last $SaO_2$ stored in $SaO_2$ memorizing table of memory section (MO) and $SaO_2$ which was measured by the previous prescribed cycles, and the program proceeds to #108. At #108, a comparison of the obtained $SaO_2$ increasing speed with the minimum limit of $SaO_2$ increasing speed manually set and indicated on indicating element (152) is made. When the obtained $SaO_2$ increasing speed is over the preset minimum limit of $SaO_2$ increasing speed, the program proceeds to #106 for resetting the apnea flag.

Now, returning to FIG. 5, upon completion of subroutine (FIG. 7) to detect apnea as shown in #18, the program proceeds to #19 to check whether the apnea flag has been set or not for detecting apnea condition or not. When apnea condition has been detected at #19, the program proceeds to #28 of FIG. 9 in which apnea alarming element (116) is illuminated at #28 and an alarm sound is generated at #29. Further a counter memorizing the total number of apnea is incremented at #30 and a timer measuring the accumulated apnea time is started at #31, and the program returns to #22 of FIG. 5.

Figure 10:
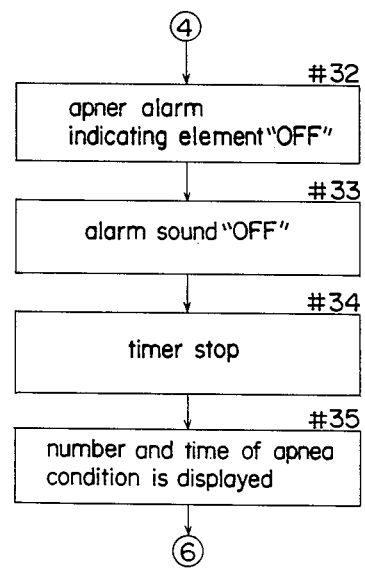

However, upon completion of the subroutine (FIG. 8) for detecting recovery from apnea as shown at #20 of FIG. 5, the program proceeds to #21. At #21, it is check whether the apnea flag has been set or not for detection of the apnea condition or not. If recovery from apnea has been detected, the program proceeds to #32 of FIG. 10. In FIG. 10, apnea alarm element (116) is turned off at #32 and an alarm sound from speaker (130) is ceased at #33. Further the timer to measure the accumulated time of apnea is stopped at #34, and indicating elements (136) and (138) indicate the total number of apnea detection and the accumulated time of apnea occurred, respectively, at #35.

When the apnea detection has not been made at #19 of FIG. 5, or when the recovery from apnea has not been made at #21, the program proceeds to #22 and waits the passage of sphygmic integration time started at #8 of FIG. 4. When the predetermined integration time has been passed, the program proceeds to #23. At #23, the integration of sphygmic integrating sections (24a) and (24b) is terminated, and the outputs are stored. Outputs from sphygmic integrating sections (24a) and (24b) and outputs from low pass filters (20a) and (20b) are A/D converted to the corresponding digital signals in turn at #24. Then, each integrating capacitors of sphygmic integarting sections (24a) and (24b) are discharged at #25 and the program returns to #4 of FIG. 4. Namely, start and completion of integration of sphygmic waves, storage of outputs, A/D conversion, and discharge of capacitors are repeated at the prescribed intervals, and the data utilized for making decisions during integrations are all based on the measured results obtained in the previous cycle.

Figure 11:
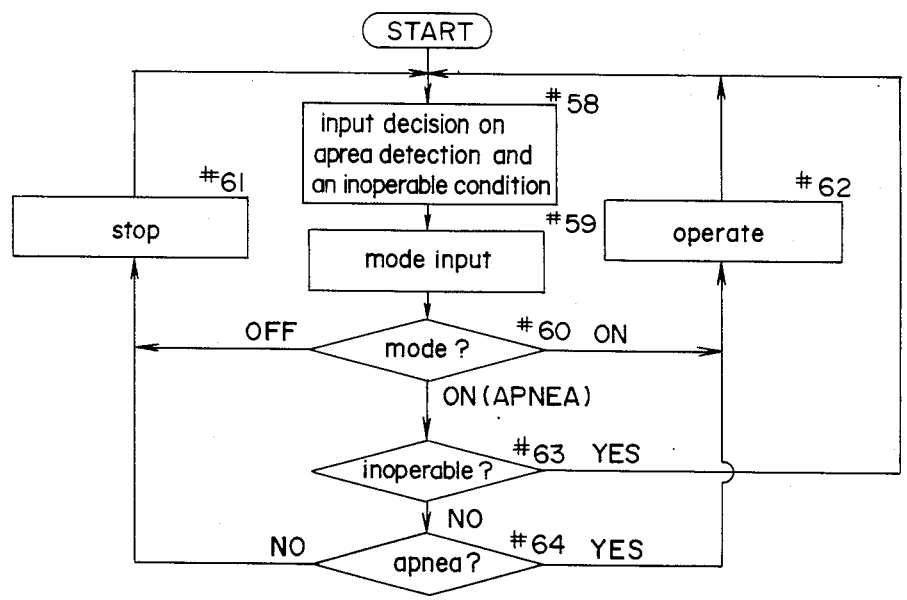

A flow chart of operation of respirator control section (48) is shown in FIG. 11. In FIG. 11, respirator control section (48) reads out the decision on apnea detection and on any inoperable condition from control processing section (30) for each measurement of $SaO_2$ and pulse rate at #58. Here, respirator switch setting section (54) has a mode setting switch (142) as shown in FIG. 3 and can select either one of the following 3 modes, namely, the mode to operate respirator (56) at all times ("ON"), the mode to operate respirator (56) only when apnea has been detected ("ON (APNEA)"), and the mode to keep respirator (56) off ("OFF"). The mode selected by this mode setting switch (142) is read out at #59 and is discriminated at #60. When the discriminated mode is the one to operate respirator (56) at all times ("ON"), the program proceeds to #62 and starts the operation of respirator (56). If a decision of inoperable condition has been given after apnea was detected at #64, respirator (56) is kept running. If recovery from apnea has been detected, respirator (56) is stopped.

In case the discriminated mode is the one to operate respirator (56) only when apnea has been detected ("ON (APNEA)", the program is separated from #60 to #63. Then, if apnea has been detected at #64, respirator (56) is operated, while respirator (56) is stopped if recovery from apnea has been detected. In this mode of operation, respirator (56) is kept running even if an inoperable condition is detected. If the discriminated mode is the one to keep respirator (56) from operating ("OFF"), the program proceeds from #60 to #61 and respirator (56) is kept off.

Figure 12:
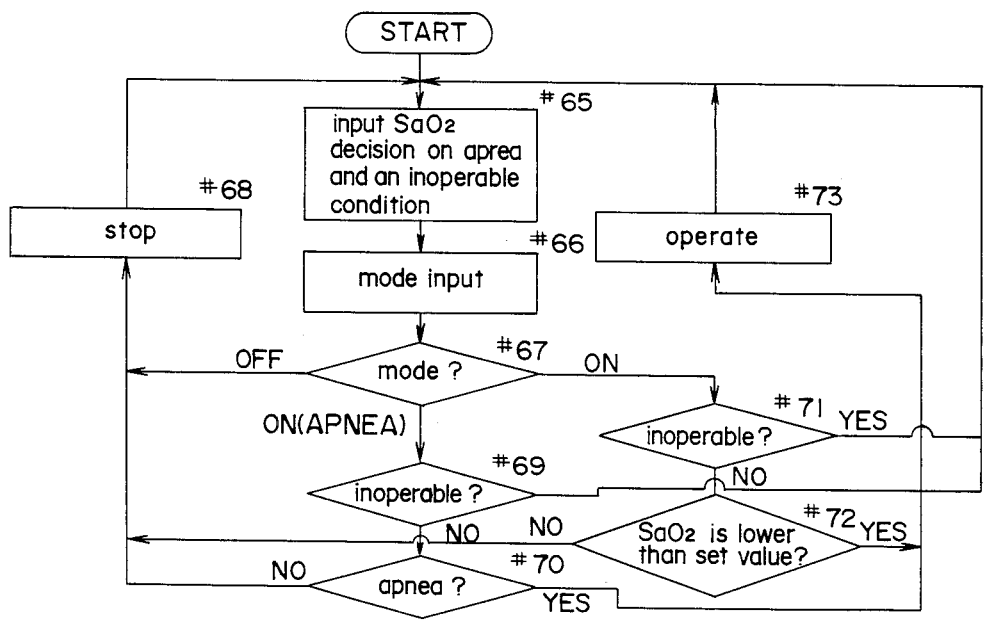

A flow chart of oxygenator control section (50) illustrated in FIG. 1 is shown in FIG. 12. In FIG. 12, oxygenator control section (50) reads the calculated $SaO_2$ and the decision on apnea detection and on inoperable condition from the CPU (30), at each measurement of $SaO_2$ and pulse rate. Oxygenator switch setting section (58) has the mode setting switch (144) and can select either one of the following 3 modes, namely, the mode to keep oxygenator (60) turned off ("OFF"), the mode to operate oxygenator (60) only when apnea has been detected ("ON (APNEA)", and the mode to operate oxygenator (60) at all times under certain condition. The mode of operation set by this switch (144) is read at #66 and is discriminated at #67. The program is separated from #67 to #69, if the mode is to operate it only when apnea has been detected ("ON (APNEA)"), and oxygenator (60) is operated at #73 when apnea has been detected at #70, while oxygenator (60) is stopped when recovery from apnea has been detected. When the mode is to keep oxygenator (60) turned off ("OFF"), the program is separated from #67 to #68 and oxygenator (60) is not operated. When the mode is to operate oxygenator (60) at all times under a certain condition ("on"), the program is separated from #67 and #71 and a comparison of the present $SaO_2$ with the $SaO_2$ value set by switches (148a) and (148b) and indicated on indicating element (146) is made. If the present $SaO_2$ is less than the set value, the program proceeds to #73 and oxygenator is operated. Further, if apnea has been detected at #70, highly concentrated oxygen inhalation is started, and when recovery from apnea has been detected oxygen concentration from inhalation is changed to normal concentration.

Figure 13:
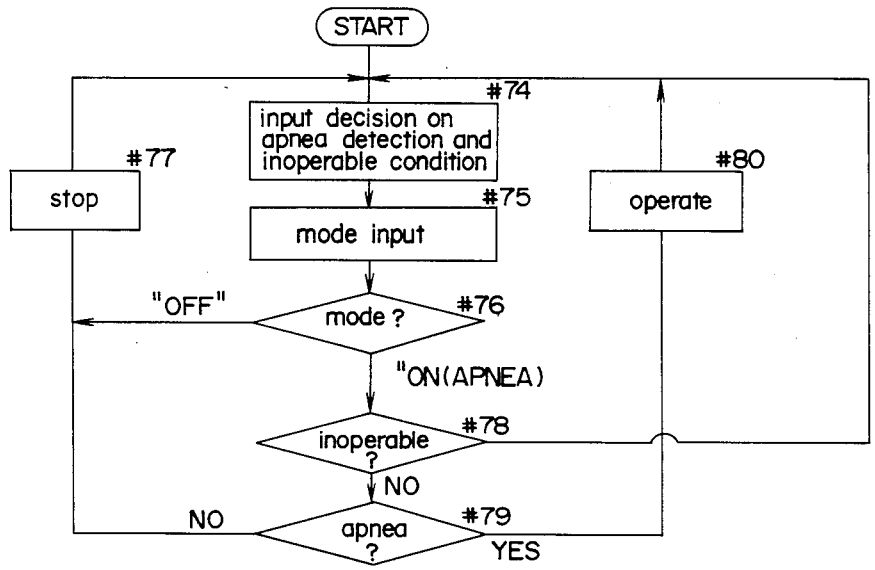

A flow chart on operation of patient stimulator control section (52) is shown in FIG. 13. Patient stimulator switch setting section (62) has the mode setting switch (150) and either the following 2 mode can be selected. Namely, there are the mode to operate patient stimulator (64) only when apnea has been detected ("ON (APNEA)") or the mode to keep patient stimulator (64) turned off ("OFF"). Decisions on apnea detection and on inoperable condition are input into patient stimulator control section (52) from control processing section (30) and the program proceeds to #75. The mode set by the switch (150) is input and at #75 the mode is discriminated at #76. If the mode to operate patient stimulator (52) only when apnea has been detected ("ON (APNEA)") has been selected, the program proceeds to #78, and return to #74 upon inputting the signal indicating inoperable condition, or proceed to #79 if the signal is not input. Operation or suspension of patient stimulator (64) is controlled at #79, depending on decisions on apnea detection and on inoperable condition which are input from control processing section (30). In other words, when apnea has been detected, the program proceeds from #79 to #80 and patient stimulator (64) is put into operation, while, when apnea has not been detected, the program proceeds to #77 and patient stimulator (84) is stopped.

Figure 14:
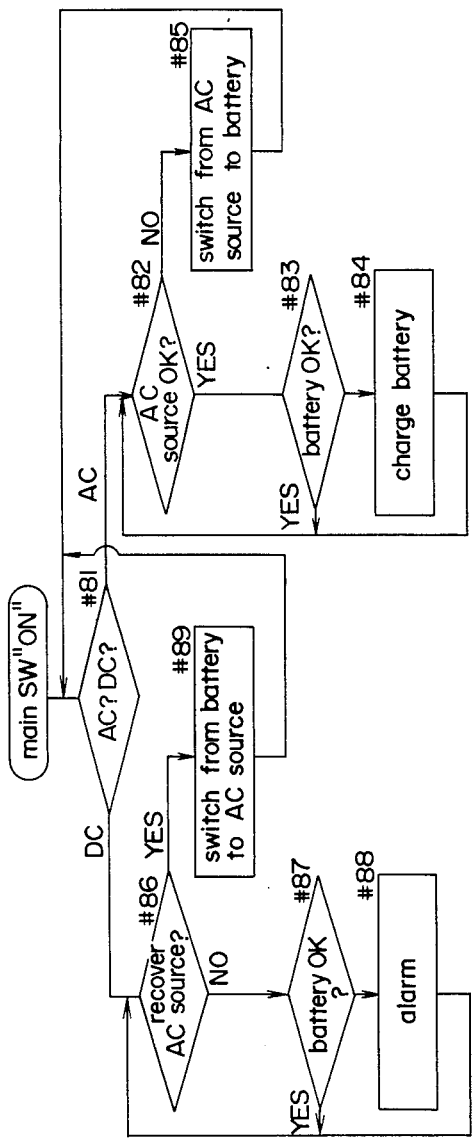

A flow chart showing the operation of main power supply (66) shown in FIG. 2 is illustrated in FIG. 14. In FIG. 14, power interruption monitoring section (72) identifies at #81, when main switch (132) is turned on, which power is supplied, AC from the AC power source (76) or DC from the built-in battery (68). When AC power source (76) is supplied, the program proceeds to #82, while it proceeds to #86 when DC is supplied from the built-in battery (68). When AC has been identified at #81, voltage of AC power source (76) is monitored at all times by power interruption monitoring section (72) at #82. When voltage drops below the prescribed value, the program is separated from #82 to #85, and the power is shifted from AC source (78) to built-in battery (68). When AC source (76) is in use, output voltage of built-in battery (68) is always detected at #83 by battery voltage detecting section (74) and once the detected voltage is lower than the required value, the program proceeds to #84 and charges the battery (68) at the battery charging section (70).

When built-in battery (68) is identified as power source at #81, power interruption monitoring section (72) monitors voltage of AC power source (76) at #86 at all times, and the program is separated to #89 to shift the power supply from built-in battery (68) to AC source (76) as soon as AC power source has recovered. When it has been detected at #87 that output voltage of built-in battery (68) has dropped lower than the required minimum level, voltage drop alarm element (122) is illuminated at #88 and alarm is given.

Next, operation in test mode is explained. Going back to FIG. 4, in #4, the setting state of the mode selector switch (134) is input. When the test mode is judged at #5, the program proceeds to #6b. At #6b, selector switches (SS) of band pass filters (14a) and (14b) select output of standard signal generating section (BS). The standard signal generating section (BS) repeatedly generates the signal in which $SaO_2$ corresponds to 95% and the signal in which $SaO_2$ corresponds to 60% at the pulse rate of 60 per minute in a predetermined cycle. Then, if the device is operated normally, the pulse rate is indicated as 60 per minute, $SaO_2$ of 95% and $SaO_2$ of 60% are alternatively indicated, and apnea alarm is operated and stopped alternatively. Thus, an operator can check the normal operation of the device by observing the above indication and alarm in the test mode.

According to the present embodiment, all alarms including apnea alarm, inoperable condition alarm, power interruption alarm, voltage lowered alarm can be transmitted from places off the apparatus though transmitter (E) and receiver (R) by means of wire or wireless communications, in addition to $SaO_2$ and pulse rate. According to the present embodiment as stated above in detail, alarm element (116) is illuminated and alarm sound is generated through speaker (130), and alarms by alarm element (84) and alarm buzzer (92) can be given from places apart from the apparatus through transmitter (E) and receiver (R), when the measured $SaO_2$ had dropped lower than the limit set by manual operation and indicated by indicating element (104) or when the $SaO_2$ lowering speed has dropped lower than the limit set by manual operation and indicated by indicating element (108), thus allowing prompt detection of apnea and relative alarms. Furthermore, according to the present embodiment, respiration and inhalation of oxygen can be carried out by operating a respirator (56) and oxygenator (80) or stimulation can be given to the patient's sole by a patient stimulator (64), in case apnea has been detected. Therefore, prompt first aid for apnea is possible with high reliability.

In the present embodiment, conditions for decision on apnea (limit values) are all designed so as to be manually set. Notwithstanding, these limits may be designed so as to be automatically set by means of processing within the apparatus. Composition and operation of the second embodiment of such composition are illustrated in FIGS. 15-18. However, any components which act in the same way as in the case of the first embodiment have been so marked with the same symbols and explanations thereabout have been omitted.

Figure 15:
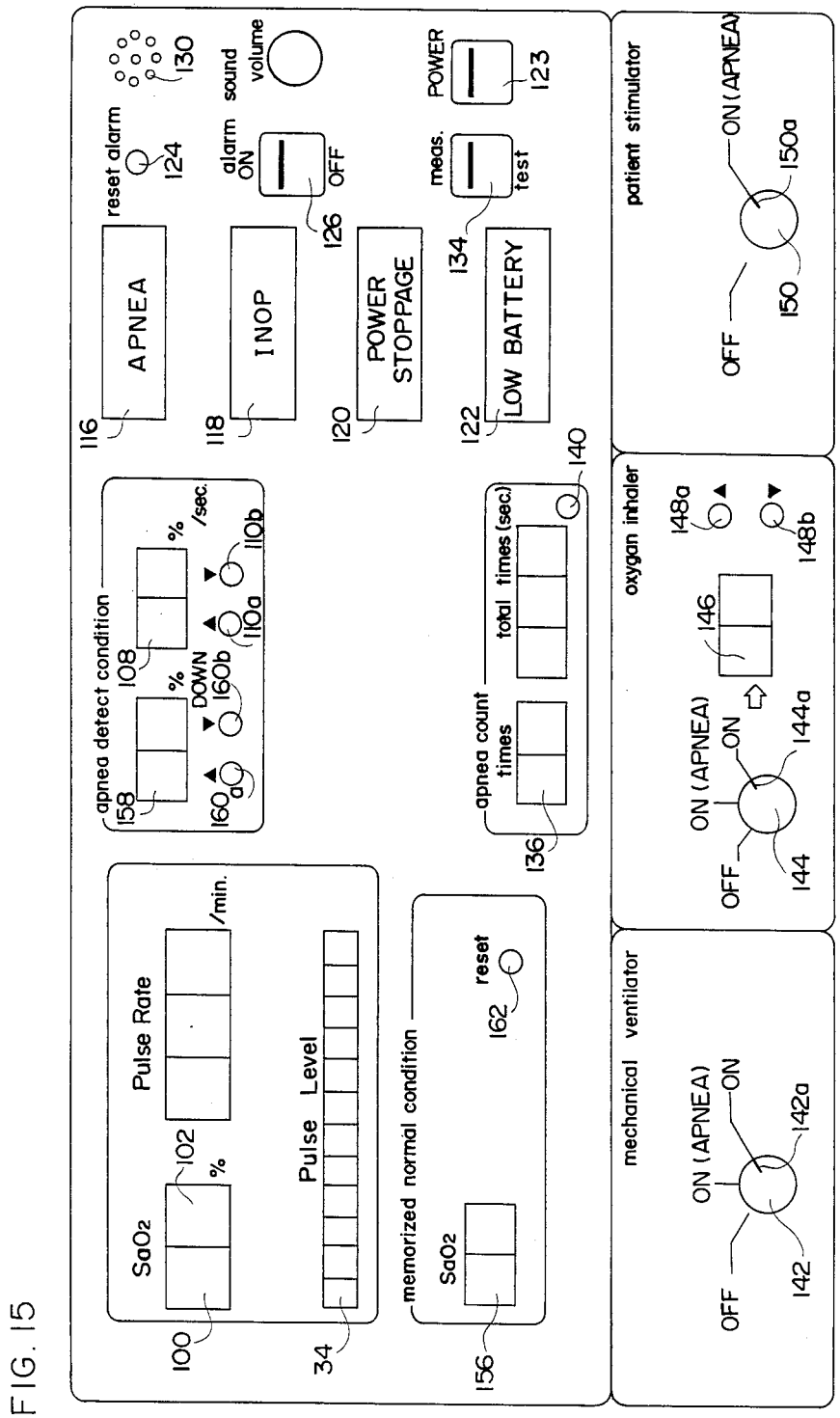

FIG. 15 shows composition of display section (44), alarm section (46) and range setting section (40) of the second embodiment and it corresponds with FIG. 3 of the first embodiment. In FIG. 15, (156) is an element indicating $SaO_2$ under normal condition, whose indicated value has been processed in control processing section (30) and is stored in memory section (MO). Different from the first embodiment shown in FIG. 3, detection of apnea in this embodiment is made by detecting that the measured $SaO_2$ is lower than the $SaO_2$ reduction amount indicated on an element (158) from the normal $SaO_2$ value indicated on the element (156). The $SaO_2$ reduction amount indicated on element (158) can be manually set by operating increment button key (160a) or decrement button (160b). In the present embodiment, detection of apnea in a case where the measured decreasing speed of $SaO_2$ becomes larger than the set value indicated on element (108) is almost the same as those shown in FIG. 1 and FIG. 2 of the first embodiment, and the composition and operation of the second embodiment are also almost the same as those of the first embodiment, as shown in flow charts of FIGS. 4-14. Therefore, only mutually different sections are illustrated in FIGS. 16-18 and explanations only thereof are given here.

Figure 16:
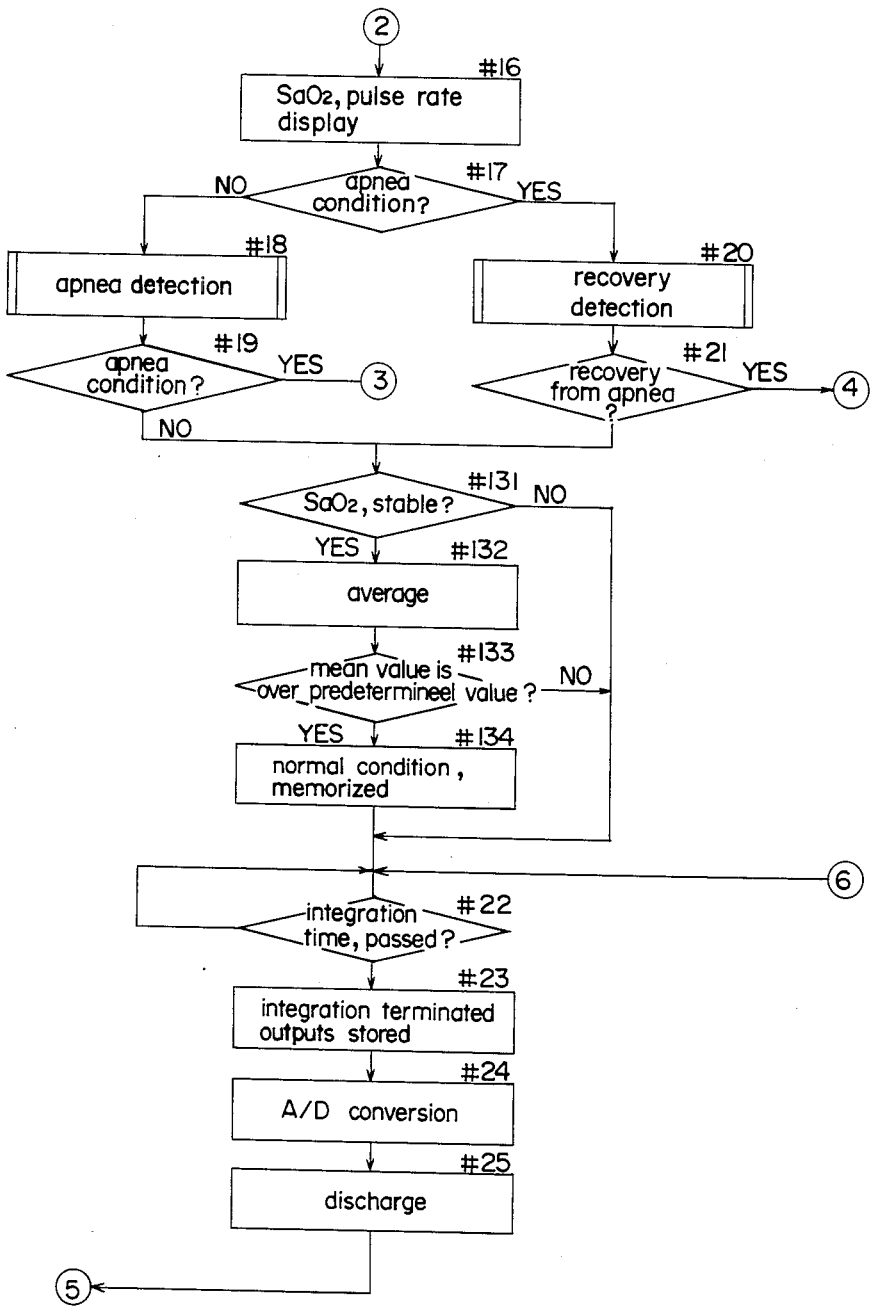
FIGS. 16–18 are flow charts showing movements of the second embodiment different from those in the first embodiment.

FIG. 16 corresponds to FIG. 5 of the first embodiment. Program proceeds from either #19 or #21 to #22 in FIG. 5, while in the second embodiment, steps #131 to #134 are inserted there. These steps are for seeking $SaO_2$ at a normal condition indicated on the element (156). At #131, within the plurality of memorized $SaO_2$ values, the latest predetermined number of $SaO_2$ values are picked up, and it is judged whether these picked up values are within a predetermined deviation range or not. Thus, it is judged whether $SaO_2$ is stable or not at #131. When it is judged as stable, the program proceeds to #132, the mean value of the picked $SaO_2$ values is calculated. A judgement is made at #133 whether the processed mean value of $SaO_2$ is above a prescribed value or not. If the mean $SaO_2$ is larger than the prescribed value, the program proceeds to #134. At #134, the processed mean value of $SaO_2$ is stored in the memory section (MO) as $SaO_2$ value at normal condition and indicated on element (156). Outputs from low pass filters (20a) and (20b) obtained are memorized in memory section (MO) in similar ways and used for measurements of the luminous intensity at #9 of FIG. 4 and detection of apnea instead of $SaO_2$. Then, the program proceeds to #22 from #134. When the picked $SaO_2$ values have been judged unstable at #133 due to an excessively wide dispersion of $SaO_2$ values, or when the mean $SaO_2$ value processed at #133 has been judged lower than the prescribed value, the program does not reset the normal value of $SaO_2$ and outputs from low pass filters (20a) and (20b) at #134, but proceeds to #22.

Figure 17:
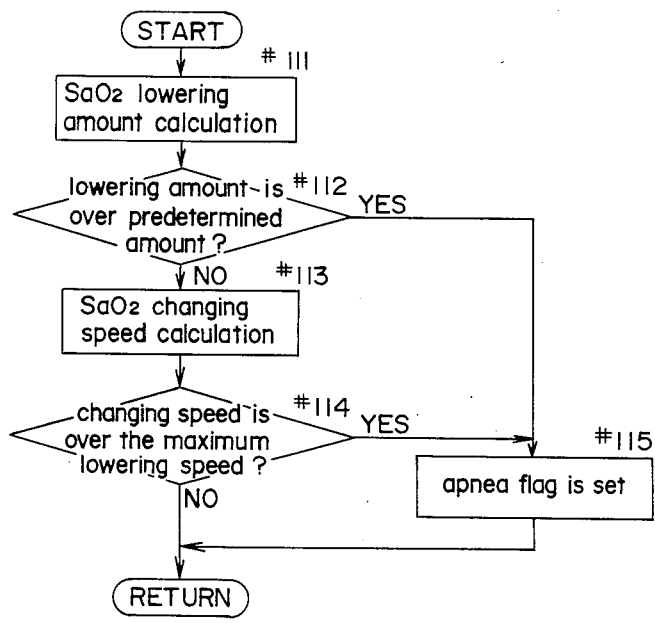

The subroutine shown at #18 of FIG. 16 is illustrated in detail in FIG. 17. In FIG. 17, the measured reduced amount of $SaO_2$ against $SaO_2$ at normal condition based on the mean $SaO_2$ is calculated at #111, and judgement is made at #112 if this amount of reduction is more than the prescribed value set on element (158) shown in FIG. 15 or not. If it is more than the prescribed amount, the program proceeds to #115 and returns after having set the apnea flag. If judged as less than the prescribed at #112, the program proceeds to #113 to process the SaO$_2$ changing speed in the same way as used in the first embodiment. At #114 judgement is made if this SaO$_2$ changing speed is larger than the value indicated on element (108) or not. If the processed SaO$_2$ changing speed is judged larger than the set value, the program proceeds to #115 and returns after having set the apnea flag, or it returns without setting the apnea flag if the SaO$_2$ changing speed is not larger than the set value.

Figure 18:
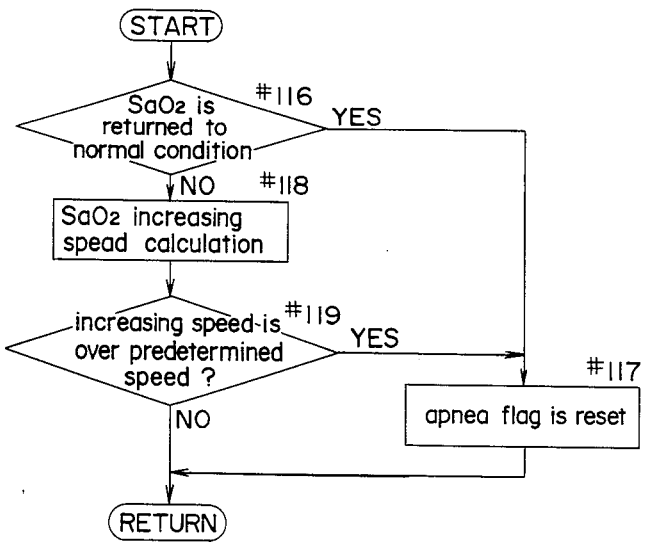

Additionally, a subroutine for judging recovery from apnea as shown at #20 of the second embodiment is illustrated in Fig. 18. In FIG. 18, it is judged at #116 whether the measured SaO$_2$ has returned to the value of the normal condition indicated on element (156) or not. When the measured SaO$_2$ has returned, the program proceeds to #117 to set the apnea flag. If it has not returned to the value of the normal condition. The program proceeds to #118 and calculates the SaO$_2$ increasing speed. If the calculated SaO$_2$ increasing speed is higher than the prescribed speed stored in memory section (MO), the program proceeds from #119 to #117 and returns after setting the apnea flag.

In this embodiment, (162) in FIG. 15 is a reset button, which can clear the value indicated on element (156) to set a new value.

According to the second embodiment as above-mentioned, the apparatus is easy to operate and is suitable for home use, as the SaO$_2$ in normal condition can be set automatically so that apnea is detected. The apparatus can be so designed as to set the values indicated on the elements (108) and (158) in FIG. 15 at the time of manufacturing of the apparatus. Then, operations of the apparatus becomes easier and more suitable for use at home.

Figure 19:
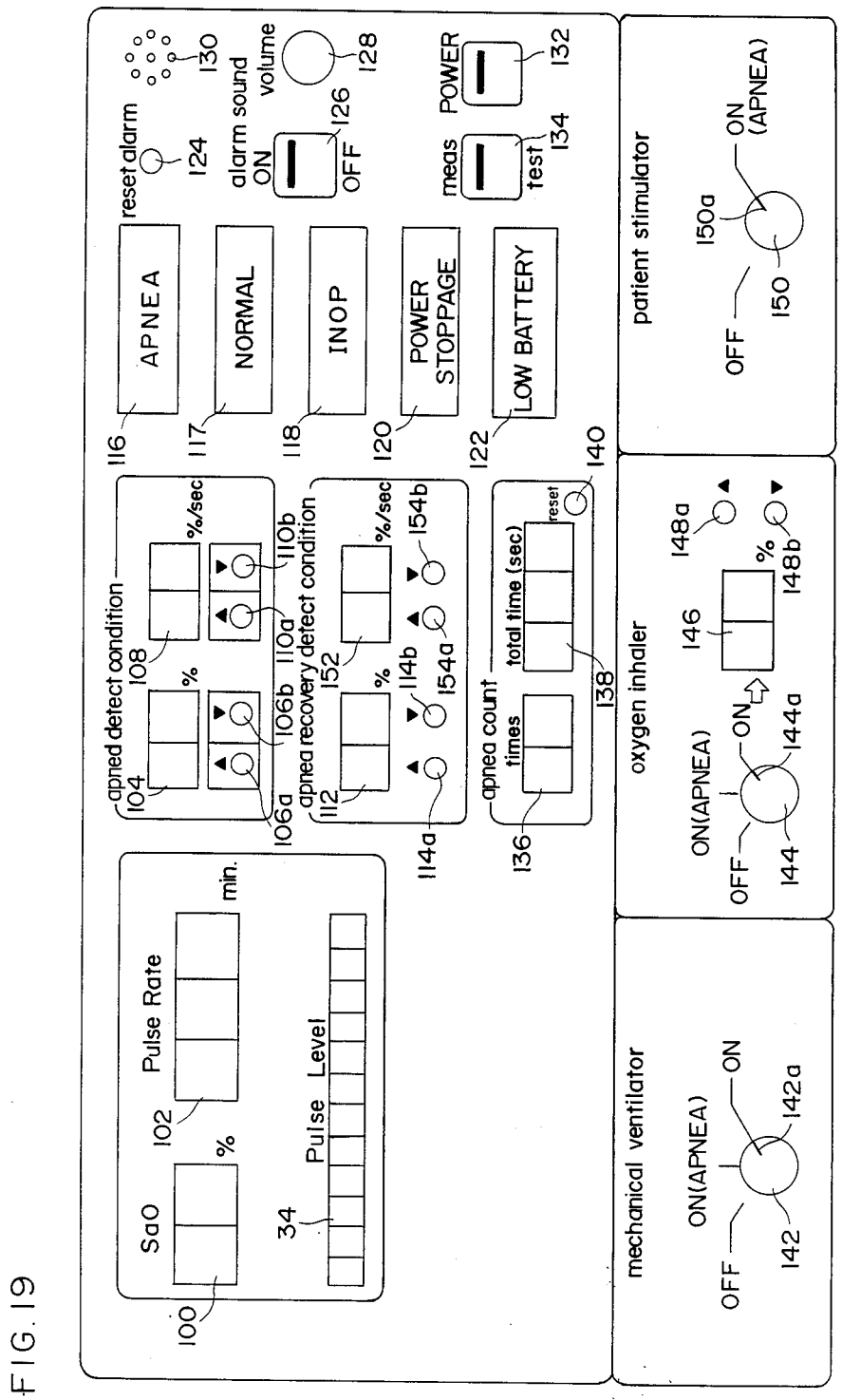
FIG. 19 is a schematic view illustrating composition of display section, alarm section and switch input section of the third embodiment.

FIG. 19 shows the display section, alarm section and range setting section of the third embodiment of the present invention. A different point in this embodiment from the first embodiment as shown in FIG. 3 is to provide a normal SaO$_2$ indicating lamp (117) which lights when the patient has recovered from apnea. When SaO$_2$ value has returned to a normal condition value after apnea was once detected, it is assumed that the patient has recovered from apnea. When the SaO$_2$ increasing speed is higher than the prescribed speed, it is also assumed that the patient has recovered from apnea and started respiration. In this embodiment, an SaO$_2$ value is employed which has been preset by the switch setting section (40) and displayed on indicating element (112) as the value showing recovery from apnea, while the SaO$_2$ increasing speed is used which has been preset by the switch setting section (40) and displayed on the indicating element (152) as the SaO$_2$ increasing speed showing recovery from apnea. Control processing section (30) judges that the patient has recovered from apnea, if SaO$_2$ has been increased at a speed higher than the rate shown on indicator (152) after it has once detected apnea, and the alarm section (46) turns off the apnea alarm element (116), and at the same time, the alarm which sounds from speaker (130) stops. When SaO$_2$ value has returned to a value higher than the value set on indicator (112), it lights up the normal SaO$_2$ indicator lamp (117).

Apnea alarm can be manually stopped through the switch (126). Operation of the third embodiment is nearly the same as those shown in the flow charts in FIGS. 4-14 of the first embodiment, but with exceptions of FIGS. 5, 7 and 8 which have slight deviations from the first embodiment. A flow chart of this embodiment corresponding to FIG. 5 is shown in FIG. 20.

Detection of apnea in this embodiment as shown at #18 of FIG. 20 takes place based on flow chart of FIG. 21 as follows: First, a comparison is made between the present SaO$_2$ and the set limit of SaO$_2$ for detecting apnea as displayed on element (104) in #101. When the present SaO$_2$ is less than the limit, the program is separated to #104 and the apnea flag is set. If the present SaO$_2$ has been detected to be higher than the limit at #101, the program proceeds to #102. Here, the changing speed of SaO$_2$ is calculated in the above described manner at #102. At #103, a comparison is made between the calculated SaO$_2$ changing speed and the limit of the SaO$_2$ lowering speed displaying on element (108). When SaO$_2$ has dropped at a speed higher than the limit, the program proceeds to #104 and the apnea flag is set. The SaO$_2$ normal flag is reset at #200.

Figure 20:
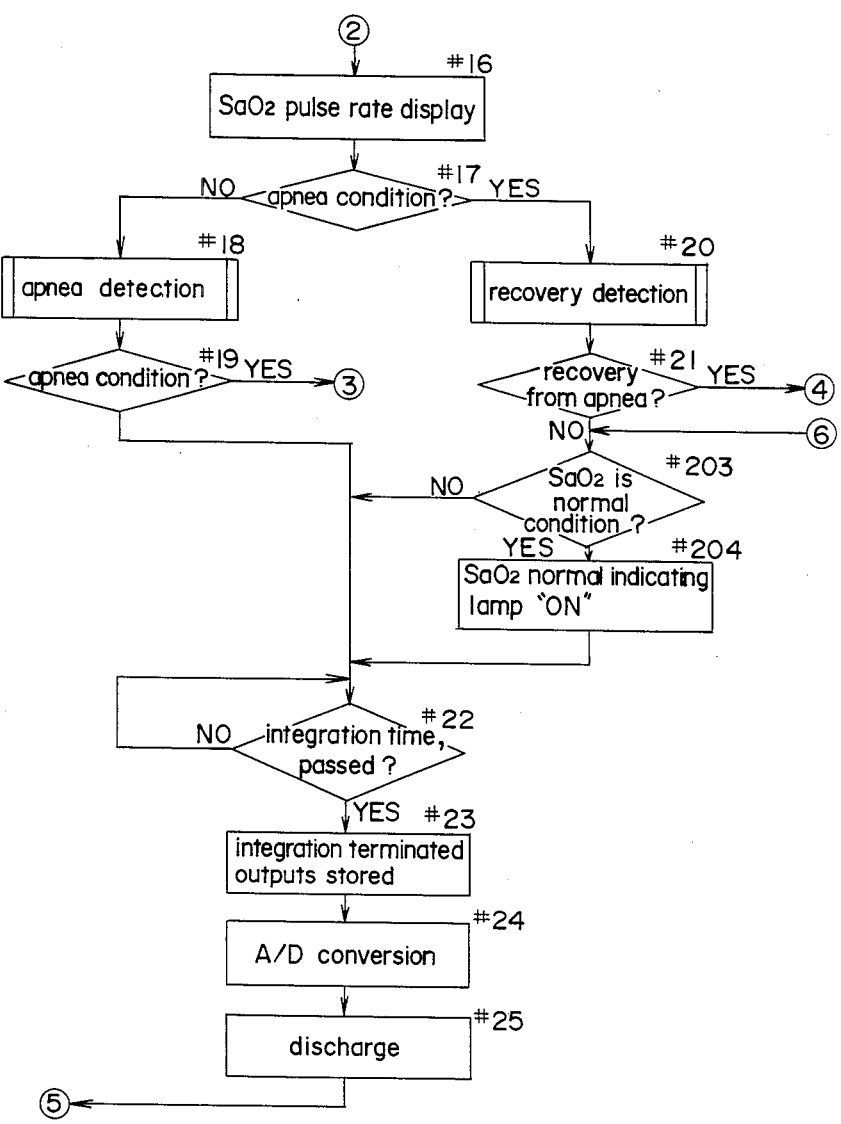
FIGS. 20–22 are flow charts showing movements of the third embodiment different from those in the first embodiment of the present invention.
Figure 21:
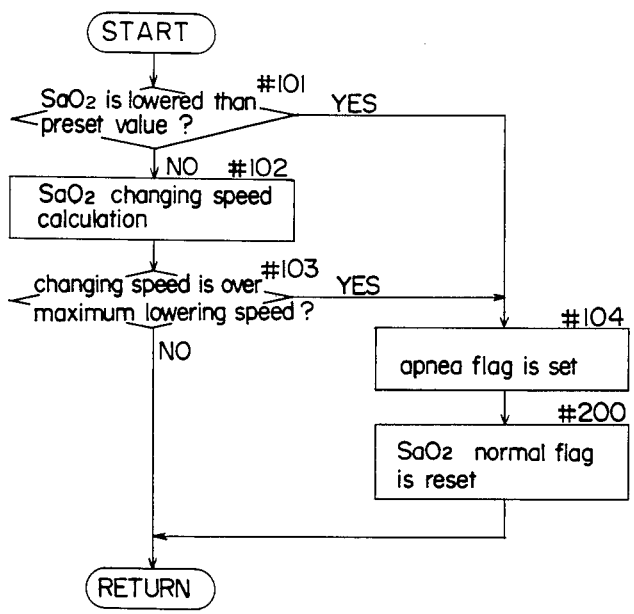
Figure 22:
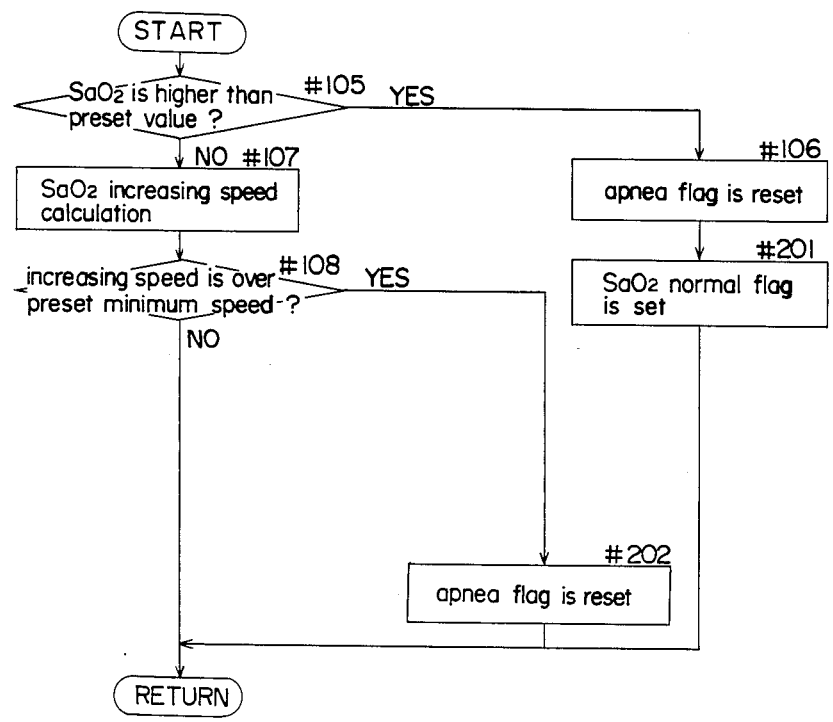

Detection of recovery from apnea in this embodiment shown in #20 of FIG. 20 is made based on the flow chart as shown in FIG. 22. In FIG. 22, a comparison is made at #105 between the present SaO$_2$ and the limit of SaO$_2$ displayed on the element (112) for detecting recovery from apnea. When the present SaO$_2$ is larger than the limit, the program proceeds to #106, and the apnea flag is set at #106 and the SaO$_2$ normal flag is reset at #201. On the other hand, when the present SaO$_2$ is less than the limit, the signals proceed to #107. At #107, the SaO$_2$ increasing speed is calculated as described above. At #108, a comparison is made between the calculated SaO$_2$ increasing speed and the limit of the speed manually preset and displayed on the element (152). When SaO$_2$ has increased at a speed higher than the limit, the program proceeds to #202 to reset the apnea flag.

Now going back to FIG. 20, when the subroutine (FIG. 21) for detecting apnea as shown at #18 is completed, the program proceeds to #19 and a decision of apnea is made by checking the apnea flag. When an decision on apnea has been made, the program proceeds to #28 of FIG. 9 and apnea alarm element (116) is turned on and apnea alarm is given at #29. Furthermore, the counter having stored a total number of apnea occurrence is incremented at #30, and the timer that measures the accumulated duration of apnea is started at #31 and returns to #22 of FIG. 20.

On the other hand, when the subroutine (FIG. 22) shown at #20 of FIG. 20 for detecting recovery from apnea has been completed, the program proceeds to #21 and a decision of recovery from apnea is made by checking if the apnea flag has been set or not. When a decision of recovery from apnea has been made, the program proceeds to #32 of FIG. 10 and apnea alarm element (116) is turned off and the alarm sound from speaker (130) is stopped. Further at #34 the timer that measures the accumulated duration of apnea is stopped and at #35 a total suspension time of apnea and the accumulated duration are displayed on elements (136) and (138) respectively.

In addition, if a decision of recovery from apnea has not been given at #21 of FIG. 20, the SaO$_2$ normal flag is checked at #203. Then, if a decision has been made that SaO$_2$ has returned to a normal value, the normal SaO$_2$ indication lamp (117) is turned on. The program can proceed to #203 of FIG. 20 from #27 of FIG. 6, #31 of FIG. 9 and #35 of FIG. 10.

When a decision of apnea has not been made at #19 of FIG. 20, the program proceeds to #22 for waiting for the sphygmic integration time to reach the prescribed completion time. When it has reached the prescribed time, the program proceeds to #23 and terminates the integration of the sphygmic integrating sections (24a) and (24b) and stores the output. Then, at #24, outputs from the sphygmic integrating sections (24a) and (24b) and outputs from low pass filters (20a) and (20b) are converted to digital signals, and discharge respective integral capacitors of sphygmic integrating sections (24a) and (24b) at #25 and return to #4 of FIG. 4. In other words, start and completion of integrating sphygmic signals, storage thereof, A/D conversion and discharge of capacitors are repeated at the prescribed frequency and data employed for making decisions during integrations are based on results of previous measurement.

Although the present invention has been fully described with reference to several preferred embodiments, many modifications and variations thereof will be now apparent to those skilled in the art, and the scope of the present invention is to be limited not by the details of the preferred embodiments described above but only by the terms of the appended claims.

What is claimed is:

1. An apnea detector comprising;
   means for measuring oxygen saturation in blood to produce a measured oxygen saturation signal indicating the measured oxygen saturation;
   means for storing a normal oxygen saturation of a normal condition to produce a normal oxygen saturation signal;
   means for storing an increasing speed of oxygen saturation;
   means for comparing the measured oxygen saturation signal with the normal oxygen saturation signal to produce a first detecting signal when the measured oxygen saturation is larger than the normal oxygen saturation stored;
   means for calculating an increasing speed of oxygen saturation based on a plurality of the measured oxygen saturation signals to produce a second detecting signal when the calculated increasing speed of oxygen saturation is higher than the stored increasing speed of oxygen saturation; and
   means for detecting recovery from apnea condition in accordance with the first and second detecting signals.

2. An apnea detector as claimed in claim 1, wherein said normal oxygen saturation storing means includes means for manually setting the normal oxygen saturation to produce a manual setting signal indicating the set oxygen saturation, and means for storing the normal oxygen saturation in accordance with the manual setting signal.

3. An apnea detector as claimed in claim 1, wherein said normal oxygen saturation storing means includes means for calculating the normal oxygen saturation based on a plurality of the measured oxygen saturation values to produce a calculated oxygen saturation signal indicating the calculated oxygen saturation, and means for storing the normal oxygen saturation in accordance with the calculated oxygen saturation signal.

4. An apnea detector as claimed in claim 1, wherein said oxygen saturation increasing speed storing means includes means for manually setting the increasing speed of oxygen saturation to produce an increasing speed setting signal indicating the set increasing speed of oxygen saturation, and means for storing the increasing speed of oxygen saturation in accordance with the increasing speed setting signal.

5. An apnea detector comprising;
   means for measuring oxygen saturation in blood to produce a measured oxygen saturation signal indicating the measured oxygen saturation;
   means for storing a normal oxygen saturation of a normal condition to produce a normal oxygen saturation signal;
   means for storing an increasing speed of oxygen saturation;
   means for calculating increasing speed of oxygen saturation based on a plurality of the measured oxygen saturation signals to produce a first detecting signal when the calculated increasing speed of oxygen saturation is higher than the stored increasing speed of oxygen saturation;
   means for comparing the measured oxygen saturation signal with the normal oxygen saturation signal stored to produce a second detecting signal when the measured oxygen saturation is higher than the stored normal oxygen saturation;
   means for detecting start of recovery from an apnea condition in response to the first detecting signal; and
   means for detecting recovery from apnea condition in response to the second detecting signal.

6. An apnea detector as claimed in claim 5, wherein said normal oxygen saturation storing means includes means for manually setting the normal oxygen saturation to produce a manual setting signal indicating the set oxygen saturation, and means for storing the normal oxygen saturation in accordance with the manual setting signal.

7. An apnea detector claimed in claim 5, wherein said normal oxygen saturation storing means includes means for calculating the normal oxygen saturation based on a plurality of the measured oxygen saturation values to produce a calculated oxygen saturation signal indicating the calculated oxygen saturation, and means for storing the normal oxygen saturation in accordance with the calculated oxygen saturation signal.

8. An apnea detector as claimed in claim 5, wherein said oxygen saturation increasing speed storing means includes means for manually setting the increasing speed of oxygen saturation to produce an increasing speed setting signal indicating the set increasing speed of oxygen saturation, and means for storing the increasing speed of oxygen saturation in accordance with the increasing speed setting signal.

* * * * *